(12) United States Patent
Lima

(10) Patent No.: US 11,311,394 B2
(45) Date of Patent: Apr. 26, 2022

(54) SYNCHRONIZED MUSCLES

(71) Applicant: Lintec of America, Inc., Richardson, TX (US)

(72) Inventor: Marcio Dias Lima, Richardson, TX (US)

(73) Assignee: LINTEC OF AMERICA, INC., Richardson, TX (US)

( * ) Notice: Subject to any disclaimer, the term of this patent is extended or adjusted under 35 U.S.C. 154(b) by 256 days.

(21) Appl. No.: 16/677,032

(22) Filed: Nov. 7, 2019

(65) Prior Publication Data

US 2020/0138605 A1    May 7, 2020

Related U.S. Application Data

(60) Provisional application No. 62/756,945, filed on Nov. 7, 2018.

(51) Int. Cl.
*A61F 2/50* (2006.01)
*F03G 7/06* (2006.01)
*A61F 2/72* (2006.01)
*D01F 6/12* (2006.01)
*A61F 2/74* (2006.01)

(52) U.S. Cl.
CPC ............... *A61F 2/72* (2013.01); *A61F 2/50* (2013.01); *D01F 6/12* (2013.01); *F03G 7/06* (2013.01); *A61F 2/744* (2021.08); *A61F 2002/5066* (2013.01)

(58) Field of Classification Search
CPC .... D01F 6/12; A61F 2/744; A61F 2/50; A61F 2002/5066; A61F 2002/5076; F03G 7/06
See application file for complete search history.

(56) References Cited

U.S. PATENT DOCUMENTS

| 11,085,426 B2 * | 8/2021 | Lima | H01H 85/04 |
| 2016/0017899 A1 * | 1/2016 | Yang | A61F 2/08 623/14.13 |
| 2016/0025079 A1 * | 1/2016 | Li | F03G 7/06 60/528 |
| 2020/0138605 A1 * | 5/2020 | Lima | E06B 9/26 |

FOREIGN PATENT DOCUMENTS

WO    WO-2017190054 A1 *  11/2017  ........... H02N 11/006

* cited by examiner

*Primary Examiner* — Bruce E Snow
(74) *Attorney, Agent, or Firm* — Greenblum & Bernstein, P.L.C.

(57) ABSTRACT

An actuator device and method of manufacturing the same that includes at least two or more panels disposed in a frame is disclosed. Each of the two or more panels include a first rotationally-actuating artificial muscle fiber section between a first contact point of the frame and a tether point located on the panel and a second rotationally-actuating artificial muscle fiber section between the tether point and a second contact point on the frame. The tether point is approximately halfway across the length of the panel. A first and second muscle support is disposed on the panel between the tether point and the first contact point. The actuator device also includes a synchronization rod attached to the at least two or more panels.

13 Claims, 3 Drawing Sheets

SYNCHRONIZED MUSCLES

CROSS-REFERENCE TO RELATED APPLICATIONS

This Application claims priority, pursuant to 35 U.S.C. § 119(e) to U.S. Provisional Application No. 62/756,945 filed on Nov. 7, 2018. The contents of which are hereby incorporated by reference in its entirety.

BACKGROUND OF INVENTION

Artificial actuator devices based on elastic polymeric fibers have a wide range of applications. Devices comprising twisted and/or coiled actuators have the advantage of low cost, high production volume, and design simplicity. Artificial actuator devices may have advantages over small motors because of the greatly simplified engineering and lower product costs.

SUMMARY OF INVENTION

In one aspect, embodiments of the invention are directed to an actuator device that includes at least two or more panels disposed in a frame. Each of the two or more panels include a first rotationally-actuating artificial muscle fiber section between a first contact point of the frame and a tether point located on the panel and a second rotationally-actuating artificial muscle fiber section between the tether point and a second contact point on the frame. The tether point is approximately halfway across the length of the panel. A first and second muscle support is disposed on the panel between the tether point and the first and second contact point, respectively. The first and second muscle supports constrain the first and second rotationally-actuating artificial muscle fibers from moving perpendicular to their length, but allow the rotationally-actuating artificial muscle fibers to rotate. The actuator device also includes a synchronization rod attached to the at least two or more panels. During operation, an electric current is applied through the first rotationally-actuating artificial muscle fibers to cause rotational actuation of the panels in one direction. An electric current through the second rotationally-actuating artificial muscle fibers causes rotational actuation of the panels in the opposite direction.

In another aspect, embodiments of the invention are directed to method of manufacturing an actuator device. The method includes disposing at least two or more panels in a frame. The manufacturing of each of the two or more panels includes disposing a first rotationally-actuating artificial muscle fiber section between a first contact point of the frame and a tether point located on the panel and disposing a second rotationally-actuating artificial muscle fiber between the tether point and a second contact point on the frame. The tether point is approximately halfway across the length of the panel. Manufacturing the panels also includes disposing a first and second muscle support on the panel between the tether point and the first contact point. The first and second muscle supports constrain the first and second rotationally-actuating artificial muscle fibers from moving perpendicular to their length, but allow the rotationally-actuating artificial muscle fibers to rotate. The method of manufacturing the actuating device also includes attaching a synchronization rod to the at least two or more panels.

Other aspects and advantages of one or more embodiments disclosed herein will be apparent from the following description and the appended claims.

DETAILED DESCRIPTION

Figure 1:
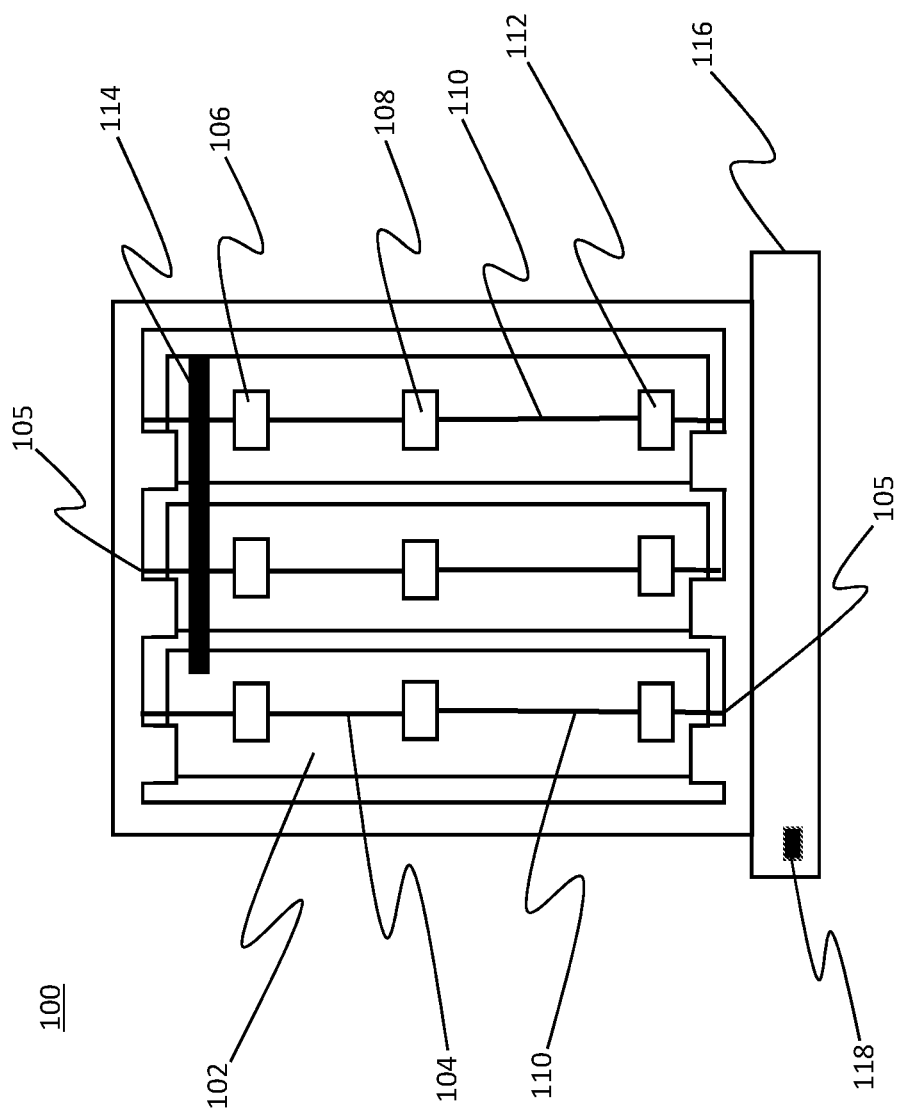
FIG. 1 is a schematic of a frame with three panels in accordance with one or more embodiments disclosed herein.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

It is to be understood that the singular forms "a," "an," and "the" include plural referents unless the context clearly dictates otherwise. Thus, for example, reference to "an artificial muscle actuator" includes reference to one or more of such artificial muscle actuators.

Terms like "approximately," "substantially," etc., mean that the recited characteristic, parameter, or value need not be achieved exactly, but that deviations or variations, including for example, tolerances, measurement error, measurement accuracy limitations and other factors known to those of ordinary skill in the art, may occur in amounts that do not preclude the effect of the characteristic was intended to provide.

In general, embodiments of the invention relate to an actuating vent and method of manufacturing an actuating vent with multiple panels that operate using artificial muscle actuators (which may also be referred to as "artificial muscle fiber" or "artificial muscle fiber section" herein) powered with electricity. In one or more embodiments, the vent is set up in such a way that the panels move in a synchronized manner to control air flow through a frame or block light from passing through the frame. Between the multiple panels may be a rigid bar that links together the multiple panels and forces all the panels to move at the same time and speed.

In one or more embodiments, each panel may include a first rotationally-actuating artificial muscle fiber section along the length of panel located between a first contact point where the fiber is attached to the frame and a tether point located in the approximate center of the panel. Each panel may also include a second rotationally-actuating artificial muscle fiber section between the tether point and a second contact point where the fiber is connected to the frame.

The first and second rotationally-actuating artificial muscle fiber sections may be formed from a single artificial muscle fiber. The first and second rotationally-actuating artificial muscle fiber sections may also be formed from two or more artificial muscle fibers connected at the tether point.

Embodiments of the artificial muscle fiber may be a fiber that is made of twist-spun polymeric fibers or nanofiber yarns. The fibers in the artificial muscle fiber may have been twisted to create a specific net bias angle with respect to the length of the artificial muscle fiber.

Upon powering the artificial muscle fiber (i.e., delivering energy to the artificial muscle fiber), the artificial muscle fiber may expand or contract, and because of the twist in the structure of the artificial muscle fiber, the expansion or contraction generates torsional and/or tensile forces (i.e., actuation). The artificial muscle fibers may be powered by delivering thermal energy to the artificial muscle fiber through radiation or electrical conduction. However, the artificial muscle fiber may be powered with other methods such as power induction, photo absorption, chemical reactions, etc.

The artificial muscle fiber may include, but is not limited to, a polymer based fiber. For example, Nylon-6, Nylon-6,6, polyethylene, polyvinylidene fluoride, Nylon-6,10, Nylon-6,12, liquid crystalline polymers such as polyarylate, and combinations thereof may be included in the artificial muscle fiber. The artificial muscle fiber may also include carbon nanotube (CNT) based materials.

The specific characteristics of the artificial muscle fiber, such as width, material, twist, actuation, etc., may vary based on the specific application for which the artificial muscle fiber is designed.

FIG. 1 is a schematic of a frame device 100 with three panels 102. In the example of FIG. 1, the frame device 100 is shown with only three panels 102; however, embodiments disclosed herein may include any number of panels.

As described above, each panel 102 may include a first rotationally-actuating artificial muscle fiber section 104 along the length of panel 102 located between a first contact point 105 (e.g., the top contact point in FIG. 1) where the fiber is attached to the frame and a tether point 108 located in the approximate center of the panel 102. Each panel 102 also includes a second rotationally-actuating artificial muscle fiber section 110 between the tether point 108 and a second contact point 105 (e.g., the bottom contact point 105) where the second rotationally-actuating artificial muscle fiber section 110 is connected to the frame device 100.

Upon actuation, the first and second rotationally-actuating artificial muscle fiber sections 104, 110 rotationally actuate in opposite directions. For example, upon actuation of the first rotationally-actuating artificial muscle fiber section 104, the first rotationally-actuating artificial muscle fiber section 104 rotates the panels 102 in a first direction to open the frame device 100, and upon actuation of the second rotationally-actuating artificial muscle fiber section 110, the second rotationally-actuating artificial muscle fiber section 110 rotates the panels 102 in a second direction opposite to the first direction to close the frame device 100.

Embodiments disclosed herein may include a first muscle support 106 or a second muscle support 112 located on each panel 102 near the contact points 105 (e.g., between the tether point 108 and the contact points 105). The first and second muscle supports 106, 112 constrain the first and second rotationally-actuating artificial muscle fibers sections 104, 110 from moving perpendicular to their length, but still allow the rotationally-actuating artificial muscle fiber sections 104, 110 to rotate. For example, the first and second muscle supports 106, 112 may have through-holes where the first and second rotationally-actuating artificial muscle fiber sections 104, 110 pass through such that the through holes do not resist rotational movements of the first and second rotationally-actuating artificial muscle fiber sections 104, 110.

In accordance with embodiments disclosed herein, different rotationally-actuating artificial muscle fiber sections 104, 110 may actuate more or less quickly than expected, causing the panels 102 to fall out of sync with each other during operation. Therefore, one or more embodiments of the frame device 100 may include a synchronization rod 114 attached to all the panels 102, ensuring a consistent actuation rate.

Figure 2:
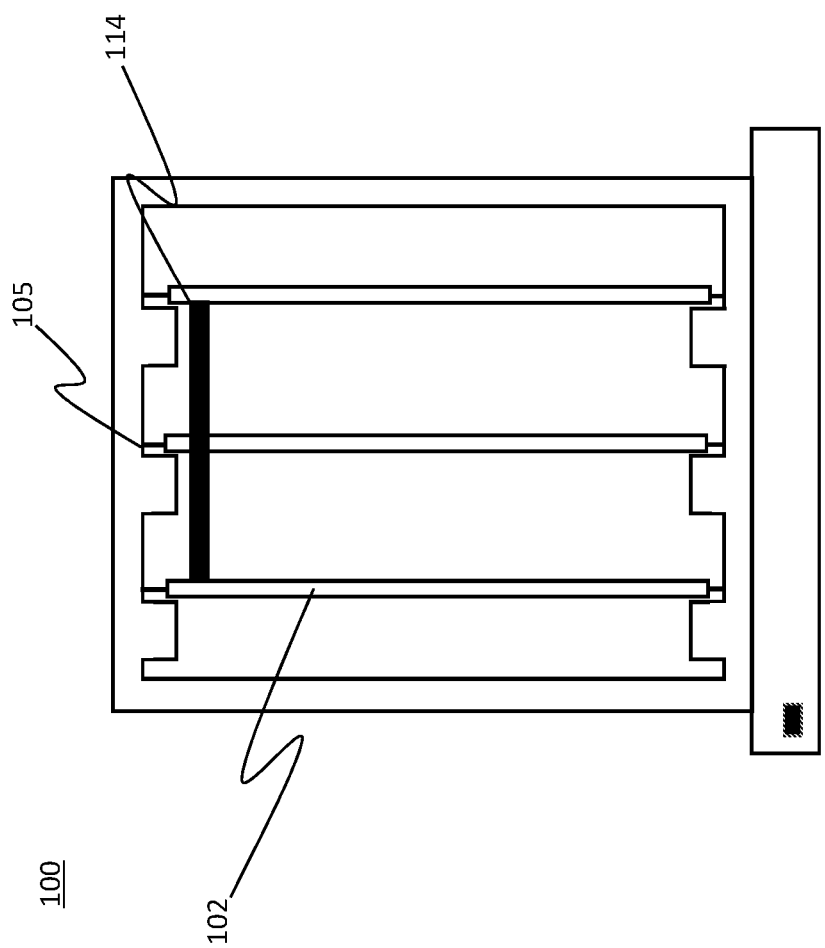
FIG. 2 is a schematic showing the panels opened within the frame in accordance with one or more embodiments disclosed herein.

Embodiments of the frame device 100 may also include a base 116 that contains the electrical components to actuate/control the panels 102 by applying an electric current through the first and second rotationally-actuating artificial muscle fiber sections 104, 110 in order to heat the sections and cause rotational actuation of the panels 102. The base includes electrical connections 118 for sending the appropriate signals to control the panels 102 in the frame device 100. For example, the electrical connections may include, but are not limited to, a connection for opening the panels 102, a connection for closing the panels 102, and/or a connection for running the frame device 100 automatically. FIG. 2 is a schematic showing the panels 102 opened within the frame device 100. The synchronization rod 114 is attached toward the edges of the panels 102 (the right-hand side edges of the panels 102 shown in FIG. 1) to avoid blocking movements of the panels 102. One of ordinary skill in the art will appreciate that the synchronization rod 114 is not limited to a particular position on the panels, but may be installed anywhere on the panel that does not interfere with the actuation of the muscle fibers.

One or more embodiments of the invention include a method of manufacturing an actuating vent (e.g., the frame device 100 shown in FIGS. 1 and 2). In accordance with embodiments, a panel is suspended on a rotational muscle fiber. The rotational muscle fiber is firmly attached to the panel only at the tether point, located approximately in the center of the panel. In accordance with embodiments, only one tether point is permitted because the space between any two tether points on a rigid surface (such as a panel) will not contribute to actuation. To keep the muscle secure panel along the length of the panel, guiding attachments, or muscle supports, are attached on the panel. The muscle supports constrain the muscle from moving perpendicular to its length, but still allow the muscle to rotate. Both ends of the rotational muscle fiber are fixed to the frame holding the panels in accordance with one or more embodiments.

Figure 3:
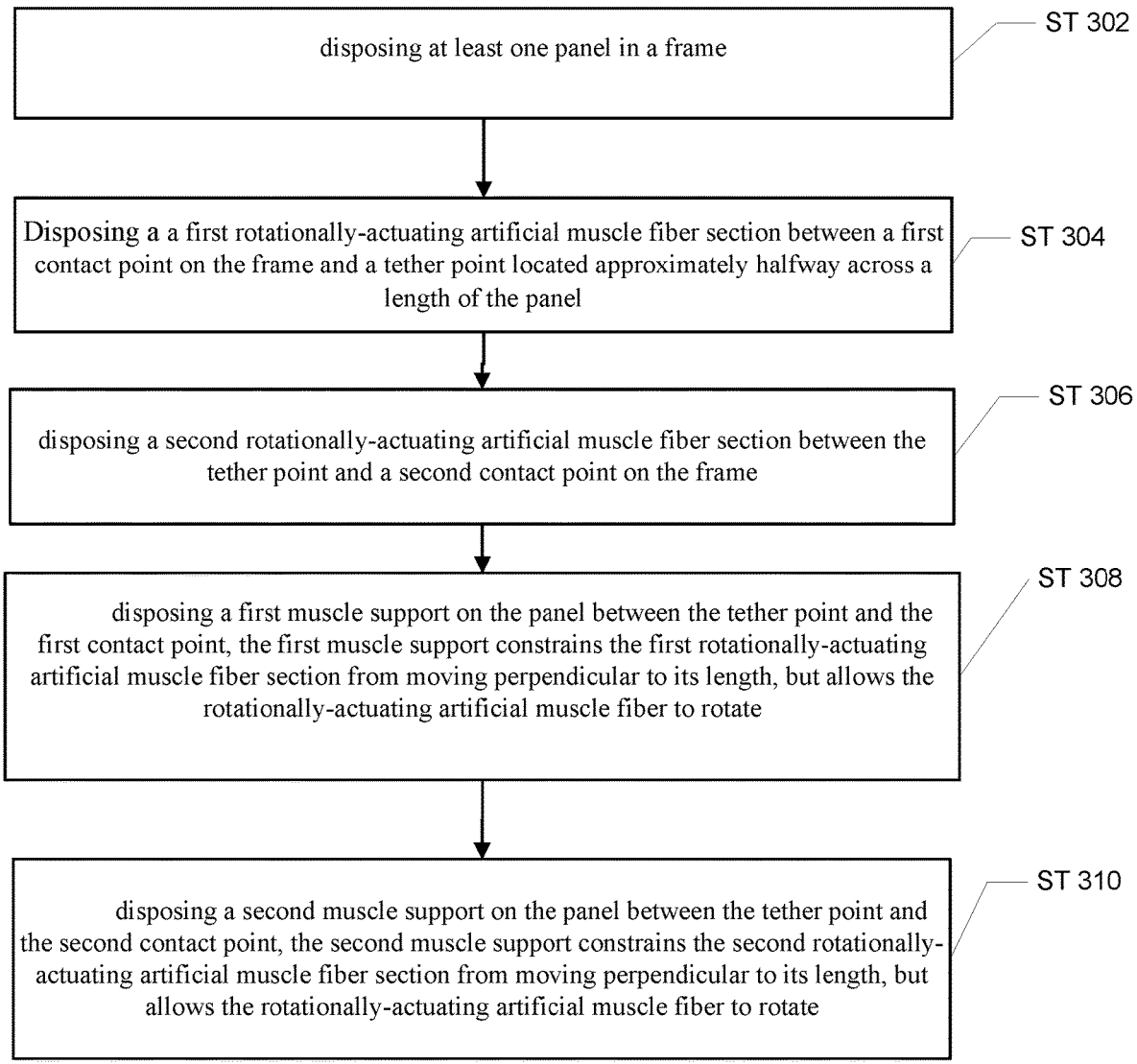
FIG. 3 is a flow chart in accordance with one or more embodiments disclosed herein.

FIG. 3 is a flow chart in accordance with one or more embodiments disclosed herein. FIG. 3 describes a method of manufacturing an actuating panel device in accordance with embodiments disclosed herein. In FIG. 3, step 302 includes disposing at least one panel in a frame. In step 304, a first rotationally-actuating artificial muscle fiber section is disposed between a first contact point of the frame and a tether point located on the panel, the tether point being approximately halfway across a length of the panel. In step 306, a second rotationally-actuating artificial muscle fiber section is disposed between the tether point and a second contact point on the frame. As previously described, embodiments may use a single rotationally-actuating artificial muscle fiber for both the first and second sections. In other words, the first and second sections may be constituted by a single artificial fiber appropriately connected at the contact points 105 and the tether point 108. Alternatively, each section may use a separate fiber.

In step 308, a first muscle support is disposed on the panel between the tether point and the first contact point and, in step 310, a second muscle support is disposed on the panel between the tether point and the second contact point. The first and second muscle supports of steps 308 and 310 constrain the first and second rotationally-actuating artificial muscle fiber sections from moving perpendicular to their length, but allow the rotationally-actuating artificial muscle fiber sections to rotate.

In accordance with embodiments disclosed herein, an electric current through the first rotationally-actuating artificial muscle fiber section causes rotational actuation of the panels in a first direction, and an electric current through the second rotationally-actuating artificial muscle fiber section causes rotational actuation of the panels in a second direction opposite to the first direction.

In one or more embodiments, the tether point and muscle supports may be disposed on the panels prior to disposing the panels into the frame and attaching the artificial muscle fibers to the frame at the contact points. As noted above, the invention is not limited to a certain number of panels. Furthermore, the invention is not limited to every panel containing an artificial muscle fiber. For example, in embodiments that include a synchronization rod, it may not be required that every panel includes an artificial muscle fiber.

In one or more embodiments, the vents are actuated/controlled by applying an electric current through the first section of the artificial muscle in order to heat that section of the muscle and cause rotational actuation of the panel. The first section refers to a section of the artificial muscle fiber located between the frame and the tether point, passing through the muscle support. When the panel has reached the apogee of its rotational motion, the electric current is stopped in the first section of muscle. By applying a current to the second section of artificial muscle fiber, which is the other section of the artificial muscle fiber located between the tether point and the frame of the vent, the panel will rotate in the opposite direction. The process may be repeated between the first and second sections of artificial muscle fiber to oscillate the panel back and forth.

In one or more embodiments, the total length of the first and second artificial muscle fiber sections is at least 12 centimeters (cm). for example, the combined length of the first and second artificial muscle fiber sections muscle is 15 cm. In accordance with embodiments disclosed herein, the longer the artificial muscle fiber, the faster and more powerful the actuation.

In the example shown in FIG. 1, the frequency of oscillation of the panels 102 may be approximately 2 Hertz (Hz), using a voltage of 12 Volts (V) to supply the required electric current for actuation. One of ordinary skill in the art will appreciate that the electric current causes the artificial muscle to heat up, causing the actuation. Accordingly, the voltage and frequency may vary based on the number and size of the panels.

Embodiments of the claimed invention may provide for a low-cost, low-voltage, and efficient vent system for controlling air flow. Embodiments of the invention may also provide for low-cost, low-voltage, and efficient automatic blind system for windows that block light and/or provide privacy.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. An actuator device comprising:
   at least one panel disposed in a frame;
   wherein each of the at least one panel comprises:
      a first rotationally-actuating artificial muscle fiber section disposed between a first contact point of the frame and a tether point located on the panel; and
      a second rotationally-actuating artificial muscle fiber section disposed between the tether point and a second contact point on the frame, wherein the tether point is disposed between the first and second contact points,
   wherein an electric current through the first rotationally-actuating artificial muscle fiber section causes rotational actuation of the at least one panel in a first direction,
   wherein an electric current through the second rotationally-actuating artificial muscle fiber section causes rotational actuation of the at least one panel in a second direction opposite to the first direction, and
   wherein the actuator device further comprises:
      at least two or more panels; and
      a synchronization rod attached to the at least two or more panels.

2. The actuator device of claim 1, further comprising:
   a first muscle support disposed on the panel between the tether point and the first contact point; and
   a second muscle support disposed on the panel between the tether point and the second contact point,
   wherein the first and second muscle supports constrain the first and second rotationally-actuating artificial muscle fiber sections from moving perpendicular to their length, but allow the rotationally-actuating artificial muscle fiber sections to rotate.

3. The actuator device of claim 1, wherein the first and second rotationally-actuating artificial muscle fiber sections are a single artificial muscle fiber.

4. The actuator device of claim 3, wherein the single artificial muscle fiber is at least 15 centimeters in length.

5. The actuator device of claim 1, wherein the electric current is supplied using no more than 12 volts.

6. The actuator device of claim 1, wherein the first or second rotationally-actuating artificial muscle fiber section comprises a polymer fiber selected from a group consisting of Nylon 6, Nylon 6,6, polyethylene, polyvinylidene fluoride, Nylon 6,10, Nylon 6,12, liquid crystalline polymers, polyarylate, and combinations thereof.

7. The actuator device of claim 1, wherein the first or second rotationally-actuating artificial muscle fiber section comprises carbon nanotubes.

8. A method of manufacturing an actuator device, the method comprising:
   disposing at least one panel in a frame;
   disposing a first rotationally-actuating artificial muscle fiber section between a first contact point of the frame and a tether point located on the panel;
   disposing a second rotationally-actuating artificial muscle fiber section between the tether point and a second contact point on the frame, wherein the tether point is disposed between the first and second contact points,
   wherein an electric current through the first rotationally-actuating artificial muscle fiber section causes rotational actuation of the at least one panel in a first direction, and
   wherein an electric current through the second rotationally-actuating artificial muscle fiber section causes rotational actuation of the at least one panel in a second direction opposite to the first direction;
   disposing at least two or more panels in the frame; and
   attaching a synchronization rod to the at least two or more panels.

9. The method of claim 8, further comprising:
   disposing a first muscle support on the panel between the tether point and the first contact point; and
   disposing a second muscle support on the panel between the tether point and the second contact point, wherein the first and second muscle supports constrain the first and second rotationally-actuating artificial muscle fiber sections from moving perpendicular to their length, but allow the rotationally-actuating artificial muscle fiber sections to rotate.

10. The method of claim 8, wherein the first and second rotationally-actuating artificial muscle fiber sections are a single artificial muscle fiber.

11. The method of claim 10, wherein the single artificial muscle fiber is at least 15 centimeters in length.

12. The method of claim 8, wherein the first or second rotationally-actuating artificial muscle fiber section comprises a polymer fiber selected from a group consisting of Nylon 6, Nylon 6,6, polyethylene, polyvinylidene fluoride, Nylon 6,10, Nylon 6,12, liquid crystalline polymers, polyarylate, and combinations thereof.

13. The method of claim 8, wherein the first or second rotationally-actuating artificial muscle fiber section comprises carbon nanotubes.

\* \* \* \* \*